(12) United States Patent
Fleenor

(10) Patent No.: US 10,561,459 B2
(45) Date of Patent: Feb. 18, 2020

(54) MULTI-FEATURE ELECTROSURGICAL INSTRUMENT

(71) Applicant: Richard P. Fleenor, Greenwood Village, CO (US)

(72) Inventor: Richard P. Fleenor, Greenwood Village, CO (US)

( * ) Notice: Subject to any disclaimer, the term of this patent is extended or adjusted under 35 U.S.C. 154(b) by 110 days.

(21) Appl. No.: 15/576,355

(22) PCT Filed: Jun. 1, 2016

(86) PCT No.: PCT/US2016/035172
§ 371 (c)(1),
(2) Date: Nov. 22, 2017

(87) PCT Pub. No.: WO2016/196562
PCT Pub. Date: Dec. 8, 2016

(65) Prior Publication Data
US 2018/0147002 A1    May 31, 2018

Related U.S. Application Data

(60) Provisional application No. 62/170,396, filed on Jun. 3, 2015.

(51) Int. Cl.
*A61B 18/14* (2006.01)
*A61B 90/30* (2016.01)
*A61B 18/00* (2006.01)

(52) U.S. Cl.
CPC .......... *A61B 18/1402* (2013.01); *A61B 90/30* (2016.02); *A61B 2018/00178* (2013.01); *A61B 2218/008* (2013.01)

(58) Field of Classification Search
CPC .................... A61B 90/30; A61B 18/14; A61B 2018/00178
See application file for complete search history.

(56) References Cited

U.S. PATENT DOCUMENTS 4,562,838 A    1/1986 Walker
4,688,569 A    8/1987 Rabinowitz
(Continued)

FOREIGN PATENT DOCUMENTS

WO    2004054626 A2    1/2004

*Primary Examiner* — Lynnsy M Summitt
*Assistant Examiner* — Tara Rose E Carter
(74) *Attorney, Agent, or Firm* — Holzer Patel Drennan

(57) ABSTRACT

An improved hand-held electrosurgical instrument includes a housing, an electrosurgical electrode, supportably interconnected to and extending from a distal end of the housing in a first direction, at least one light source supportably interconnected to the housing for emitting light in the first direction, and a light tunnel member extending away from the distal end of the housing in the first direction and defining a light tunnel therethrough for receiving and directing light emitted by the light source(s) through the light tunnel and out of a distal end of the light tunnel member. The light tunnel member yields improved tissue site illumination. The electrosurgical electrode may extend through and beyond the distal end of the light tunnel member, wherein the light tunnel extends along at least a majority of a length of the electrosurgical electrode that extends distally from the housing. The light tunnel may include an open passageway that extends proximally from the distal end of the light tunnel member for use in evacuating smoke from a tissue site. The hand-held electrosurgical instrument may include a smoke evacuation passageway fluidly interconnected to and extending proximally from the open passageway of the light tunnel, wherein smoke may be drawn in to a distal end of the open passageway, and through the open passageway and smoke evacuation passageway, to yield improved tissue site visibility and an improved working environment. The smoke evacuation passageway may be defined by a tubular member adjoined to the light tunnel member for handling as a single unit.

19 Claims, 9 Drawing Sheets

(56) References Cited

U.S. PATENT DOCUMENTS

| | | |
|---|---|---|
| 5,061,268 A | 10/1991 | Fleenor |
| 5,098,430 A | 3/1992 | Fleenor |
| 5,246,440 A | 9/1993 | Van Noord |
| 5,306,238 A | 4/1994 | Fleenor |
| 5,484,435 A | 1/1996 | Fleenor |
| 5,843,080 A | 12/1998 | Fleenor |
| 6,053,910 A | 4/2000 | Fleenor |
| 6,083,221 A | 7/2000 | Fleenor |
| 6,214,000 B1 | 4/2001 | Fleenor |
| 6,454,764 B1 | 9/2002 | Fleenor |
| 6,562,032 B1 | 5/2003 | Ellman |
| 6,648,902 B2 | 11/2003 | Colgan |
| 6,666,859 B1 | 12/2003 | Fleenor |
| 7,083,601 B1 | 8/2006 | Cosmescu |
| 7,166,102 B2 | 1/2007 | Fleenor |
| 7,367,971 B2 | 5/2008 | Fleenor |
| 8,690,872 B2 | 4/2014 | Jayaraj |
| 8,882,768 B2 | 11/2014 | Greep |
| 2007/0049927 A1 | 3/2007 | Saltzman |
| 2009/0076504 A1 | 3/2009 | Schnitzler |
| 2009/0209979 A1 | 8/2009 | Yates |
| 2010/0145333 A1* | 6/2010 | Dethier .............. A61B 18/1402 606/42 |
| 2012/0111624 A1 | 5/2012 | Maeda |
| 2012/0283728 A1* | 11/2012 | Cosmescu .............. A61B 90/35 606/46 |
| 2014/0276763 A1* | 9/2014 | Greep ................ A61B 18/1402 606/34 |
| 2014/0293590 A1* | 10/2014 | Pathy ....................... F21L 4/02 362/119 |

\* cited by examiner

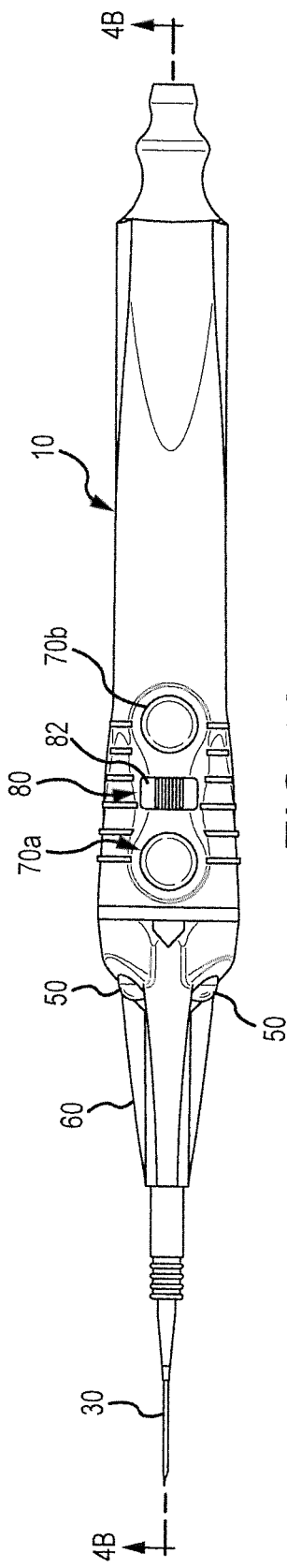
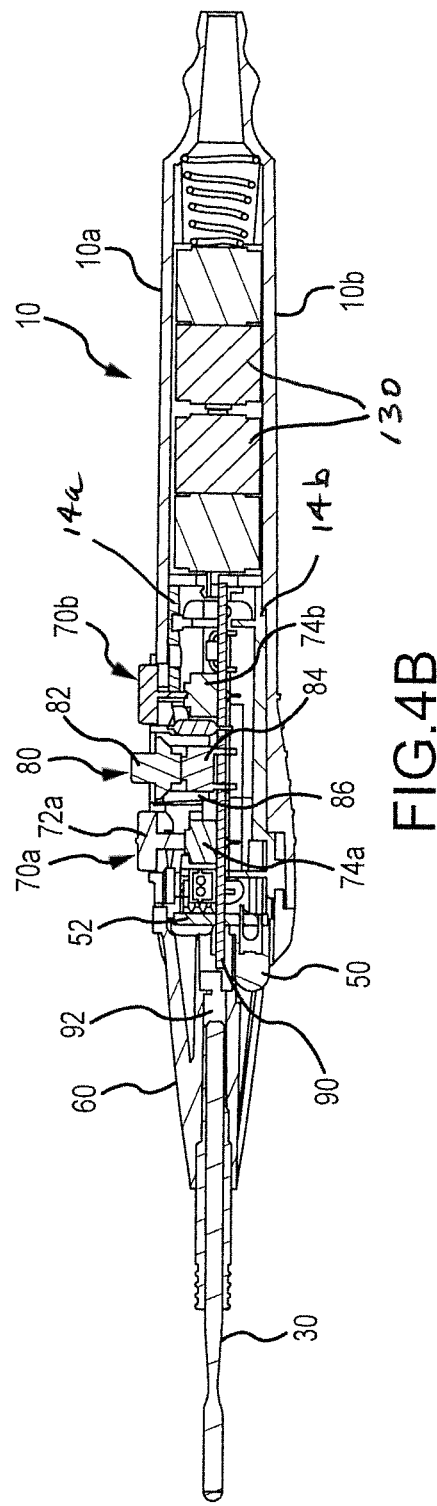

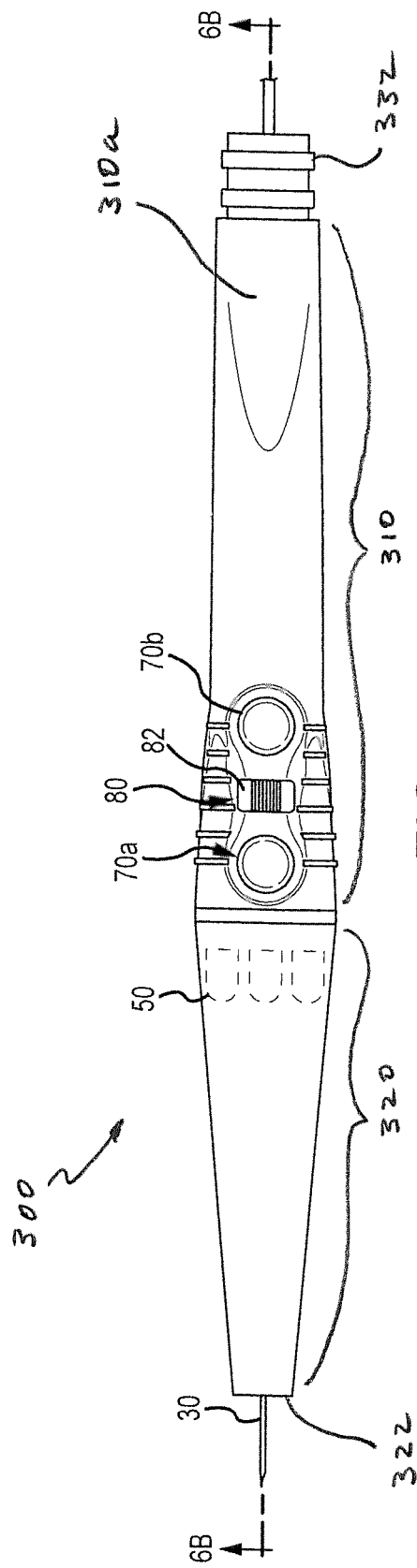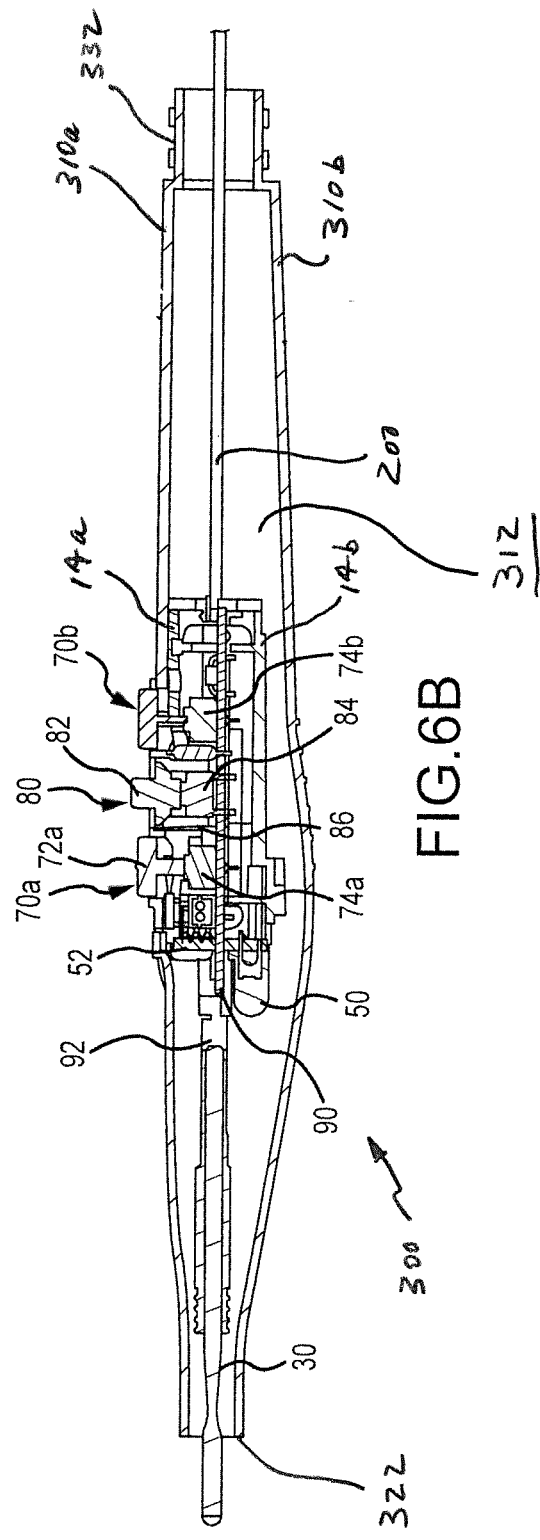
FIG.6A
FIG.6B

MULTI-FEATURE ELECTROSURGICAL INSTRUMENT

RELATED APPLICATIONS

This application claims benefit of priority to U.S. Provisional Patent Application No. 62/170,396, filed Jun. 3, 2015, entitled "MULTI-FEATURE ELECTROSURGICAL INSTRUMENT", and relates to co-pending U.S. patent application Ser. No. 14/561,082, filed Dec. 4, 2014, entitled "HAND-HELD SMOKE EVACUATION INSTRUMENT", and co-pending U.S. patent application Ser. No. 14/997,911, filed Jan. 18, 2016, entitled "HAND-HELD ELECTROSURGICAL INSTRUMENT", all of which applications are incorporated herein by reference in their entirety.

FIELD OF THE INVENTION

The present invention relates to electrosurgical instruments, and more particularly, to hand-held electrosurgical instruments that provide enhanced tissue site illumination.

BACKGROUND OF THE INVENTION

Electrosurgical procedures entail the application of an electrosurgical signal (e.g. radio-frequency electrical energy) to cut tissue and/or to coagulate tissue. The electrosurgical signal is generated by an electrosurgical generator and provided to an electrosurgical instrument having an active electrode for transferring electrosurgical energy to a tissue site to achieve a surgical effect. In turn, electrical energy is returned to the electrosurgical generator via a return electrode pad positioned under a patient (i.e. a monopolar system configuration) or by a return electrode positionable in bodily contact at or immediately adjacent to the surgical site (i.e. a bipolar system configuration).

As electrosurgical technology has evolved, increased surgical precision is realizable. To take full advantage of enhanced electrosurgical techniques, however, improved visibility of a tissue site is desirable. In that regard, illumination of a tissue site may be provided by directable overhead lighting. Additionally, or alternatively, head lamps and/or separate hand-held lighting devices may be employed by medical personnel. Known approaches have limitations in relation to their ability to conveniently illuminate a tissue site with an adequate amount of light and without shadowing affects that result from the presence of obstructions between a light source and a tissue site (e.g. an active electrode).

In the later regard, optimal tissue site illumination may be complicated by the generation of smoke attendant to electrosurgical procedures. In that regard, tissue resistance to the passage of electrical energy at a surgical site results in rapid tissue heating. In turn, tissue thermal denaturation, desiccation, and/or vaporization may occur, thereby yielding significant smoke that may obstruct surgical site illumination.

Further, patient and medical personnel health risk considerations attendant to such smoke generation are of growing concern. Indeed, research indicates volatile organic and/or polycyclic compounds present in electrosurgical smoke may include formaldehyde, acetaldehyde and toluene. Additional undesirable particulate matter may also be present, and there is concern that such smoke constituents cannot be adequately addressed by breathing masks and the like.

SUMMARY OF THE INVENTION

An object of the present invention is to provide an electrosurgical instrument that provides enhanced tissue site illumination.

A further object is to provide an electrosurgical instrument that is easy to manipulate.

Another object is to provide an electrosurgical instrument that facilitates smoke evacuation from a surgical tissue site.

An additional object is to provide an electrosurgical instrument that is employable with conventional electrosurgical generators.

Yet a further object is to provide an electrosurgical instrument that does not have additional and/or non-conventional power requirements.

In one embodiment, an improved hand-held electrosurgical instrument is provided that includes a housing configured for hand-held use, an electrosurgical electrode supportably interconnected to and extending away from a distal end of the housing in a first direction, and at least one light source supportably interconnected to the housing for emitting light in the first direction. Further, the hand-held instrument may include a light tunnel member, interconnected or interconnectable to the housing, extending away from the distal end of the housing in the first direction and defining a light tunnel for receiving and directing light emitted by the light source(s) through the light tunnel and out of a distal end of the light tunnel member.

The provision of a light tunnel member advantageously provides for illumination of a volume located distal to the distal end of the light tunnel member, wherein illumination obstruction of a tissue site is minimized. In turn, the illuminated volume provides improved viewing of a tissue site during electrosurgical procedures at the tissue site.

By way of example, the emitted light from the light source(s) may be a light beam(s) having a center axis parallel to or substantially parallel to (e.g. within 20°) a central axis of an elongated electrosurgical electrode, and having relatively low beam divergence. Further, the central axis of the elongated electrosurgical electrode may be parallel to or aligned with a longitudinal axis of the housing.

In some embodiments, the electrosurgical electrode extends through at least a portion of the light tunnel of the light tunnel member. For example, the electrosurgical electrode may extend through and beyond the light tunnel at the distal end of the of the light tunnel member. In some implementations, the light tunnel member may extend along at least a majority of a length of the electrosurgical electrode that extends distally from the housing, and in some instances, the light tunnel member may extend along at least 70% of the length of the electrosurgical electrode that extends distally from the housing.

The light tunnel member may be provided so that the light tunnel comprises an open passageway and/or a solid, light-transmissive material. In either case, the light tunnel functions to direct the light emitted by the light source(s) through the light tunnel and out of the distal end of the light tunnel member for enhanced tissue site illumination. Further in that regard, all or a portion of an outer surface of the light tunnel member and/or all or a portion of an internal sidewall defining an open passageway of the light tunnel may be optionally treated to increase the directing of emitted light to the distal end of the light tunnel member. For example, reflective coatings and the like may be employed.

In some embodiments, a proximal end portion of the light tunnel member may extend over all or at least a portion of the light source(s), e.g. to define a shroud. In some arrangements, at least the proximal end portion of the light tunnel member comprises a material that is light transmissive and that is configured so that at least a portion thereof abuts at least a portion of the light source(s).

In contemplated implementations, a plurality of light sources may be interconnected to the housing for emitting light in the first direction, wherein the plurality of light sources are disposed at circumferentially offset locations about a longitudinal axis of the housing (e.g. an axis that is aligned with or parallel to a central axis of an elongated electrosurgical electrode) so as to reduce or substantially eliminate shadowing effects of the electrosurgical electrode within the illuminated volume (e.g. at least two light sources offset 180°). In some implementations, N light sources may be provided, wherein N≥3 and the circumferentially offset locations of adjacent ones of the N light sources are offset by at least A°, wherein: A°=180°/N−1. The light emitted by the light sources may be light beams that each have a center axis parallel to or substantially parallel to (e.g. within 20°) a central axis of an elongated electrosurgical electrode, and having relatively low beam divergence.

In some embodiments, the light tunnel may include an open passageway that extends proximally from the distal end of the light tunnel member. For example, the light tunnel member may be tubular so as to define the open passageway therethrough. In turn, a proximal end of the open passageway may be fluidly interconnectable to a vacuum generator to draw gas through the distal end to provide for smoke evacuation at a tissue site. In such embodiments, the light tunnel member may perform dual functions, i.e. directing light outward through the open passageway in a first direction through the distal end, and drawing smoke inward through the distal end for evacuation through the open passageway in an opposite direction. Such bi-directional, dual functionality of the light tunnel member yields combinative benefits while maintaining a low profile.

In one approach, the hand-held instrument may further include a smoke evacuation passageway fluidly interconnected to and extending proximally from the open passageway of the light tunnel of the tubular distal end portion of the light tunnel member. As such, a continuous gas passageway may be provided between a distal of the light tunnel member and a proximal end of the smoke evacuation passageway.

A proximal end of the smoke evacuation passageway may comprise an interconnection port that is interconnected or interconnectable to a gas conduit having a proximal end interconnected or interconnectable to a vacuum generator. Upon operation of the vacuum generator, smoke generated at a surgical tissue site may be advantageously drawn through a distal end of the open passageway of the light tunnel member, through the smoke evacuation passageway, and through the gas conduit to the vacuum generator.

In one approach, a tubular member may be provided at a proximal end of the light tunnel member and may define all or at least a portion of the smoke evacuation passageway therethrough. In contemplated implementations, the light tunnel member and tubular member may be adjoined for handling as a single unit. The smoke evacuation passageway may extend through the tubular member from a distal end to an interconnection port provided at a proximal end of the tubular member. In some arrangements, the tubular member may include an outer surface portion (e.g. a concave outer surface portion) configured to conformally engage (e.g. to cradle) an outer surface portion (e.g. a convex surface portion) along a bottom side of the housing of the hand-held instrument.

Optionally, the light tunnel member may comprise at least one clip member for selective interconnection of the light tunnel member to and disconnection of the light tunnel member from the housing of the hand-held instrument. By way of example, the light tunnel member may include a first clip member, adjoined to and extending proximally from the light tunnel member for selective interconnection of light tunnel member to the distal end of the housing. Further, a second clip member may be adjoined to and extend laterally from a proximal end of the tubular member for selective interconnection of the tubular member to and disconnection of the light tunnel member from the housing.

In other arrangements, the smoke evacuation passageway may extend through all or at least a portion of the housing. For example, the housing may include an internal tubular member having a distal end fluidly interconnected to the open passageway of the light tunnel member and a proximal end fluidly interconnected to the interconnection port.

In another approach, the housing may define the smoke evacuation passageway extending therethrough, wherein a distal end of the housing is adjoined to the proximal end of the light tunnel member and fluidly interconnected to the open passageway of the light tunnel of the tubular distal end portion of the light tunnel member. As such, a continuous gas passageway may be provided between the distal end of the light tunnel member and a proximal end of the housing (e.g. a proximal end having an interconnection port that is interconnected or interconnectable to a gas conduit having a proximal end interconnected or interconnectable to a vacuum generator). In some implementations, the light tunnel member and housing may be defined together by interconnected, opposing members (e.g. a top member and a bottom member) that each extend from the distal end of the light tunnel to the proximal end of the housing.

In some embodiments, the hand-held electrosurgical instrument may include at least one battery electrically interconnectable to the light source(s) to power the light source(s) (e.g. via a light switch), wherein the light source(s) is operable to emit light free from interconnection to an external energy source. In some arrangements, the at least one battery is supportably disposed within the housing of the hand-held electrosurgical instrument. In other implementations, the hand-held electrosurgical instrument may include an electrical signal line (e.g. electrical cabling) having a proximal end electrically interconnected to the at least one battery and a distal end electrically interconnectable to the light source(s) (e.g. via a light switch). Further, a battery support member may be provided that is physically interconnected to the electrical interconnection line at the proximal end thereof, wherein the at least one battery is supportably positionable within and removable from the battery support member.

In other embodiments, as opposed to the inclusion of one or more batteries for powering the light source(s), the hand-held surgical instrument may include an electrical signal line having a proximal end electrically interconnectable to an external power source and a distal end electrically interconnectable to the light source(s) (e.g. via a light switch). For example, the proximal end of the electrical signal line may include an AC to DC adapter plug.

In some arrangements, the hand-held electrosurgical instrument may include a first electrical signal line comprising a plurality of electrical conductors (e.g. three wires) with a proximal end that includes a three-prong plug for electrical interconnection with an electrosurgical generator, and a distal end electrically interconnectable to the electrosurgical electrode. In the later regard, the hand-held electrosurgical instrument may include a first signal switch interconnected to the housing and manipulatable to control on/off delivery of a first electrosurgical signal (e.g. a tissue cutting signal) from an electrosurgical generator via the first electrical signal line to the electrosurgical electrode. Further, the hand-held electrosurgical instrument may include a second signal switch interconnected to the housing and manipulatable to control on/off delivery of a second electrosurgical signal (e.g. a tissue coagulation signal) from an electrosurgical generator via the first electrical signal line to the electrosurgical electrode.

In some embodiments, the hand-held electrosurgical instrument may include a second electrical signal line having comprising a plurality of electrical conductors with a proximal end that is electrically interconnected or interconnectable to at least one battery and/or that is electrically interconnected or interconnectable to an external power source, and having a distal end electrically interconnectable to a light source(s) via a manually controllable on/off light switch. In one arrangement, the light switch may be located in line and between the first signal switch and second signal switch along a portion of the housing of the hand-held electrosurgical instrument.

In another embodiment, a method of operation an electrosurgical instrument may include the steps of providing an electrosurgical signal to an electrosurgical electrode of an electrosurgical instrument, wherein the electrosurgical electrode extends in a first direction from a housing of the hand-held electrosurgical instrument, and supplying a power signal to one or more light source(s) of an electrosurgical instrument, wherein the light source(s) emits light in the first direction. The method may further include the step of receiving the emitted light in a light tunnel of a light tunnel member of the electrosurgical instrument, wherein the light tunnel member extends along the electrosurgical electrode in the first direction, and wherein the light tunnel directs the emitted light through the light tunnel and out of the distal end of the light tunnel member. As may be appreciated, the method embodiment advantageously provides for improved illumination of a volume located distal to the distal end of the light tunnel member.

Further in that regard, the electrosurgical instrument employed in the method embodiment may be provided so that the electrosurgical electrode extends through at least a portion of the light tunnel of the light tunnel member. Further, the electrosurgical electrode may extend through and beyond the distal end of the light tunnel member. Additionally, the light tunnel of the light tunnel member may be provided to extend along at least a majority of a length of the electrosurgical electrode that extends from the housing.

In the method embodiment, the supplying step may include supplying the power signal to a plurality of light sources of the electrosurgical instrument, wherein each of the plurality of light sources emits light in the first direction, wherein the plurality of light sources comprise N light sources that are disposed at circumferentially offset locations about a longitudinal axis of said housing, wherein N≥3 and the circumferentially offset locations of adjacent ones of the N light sources are offset by at least A °=180°/N−1. Further, the light emitted by the light sources may be light beams that each have a center axis parallel to or substantially parallel to (e.g. within 20°) a central axis of the electrosurgical electrode.

In conjunction with the method embodiment, the light tunnel of the light tunnel member of the electrosurgical instrument may include an open passageway that extends through the light tunnel member from the distal end to a proximal end thereof. In turn, the method embodiment may include the step of drawing gas through the open passageway at the distal end of the light tunnel member. Further, the electrosurgical instrument may include a smoke evacuation passageway fluidly interconnected with the open passageway of the light tunnel member, wherein the method embodiment may further include flowing the gas from the open passageway through the smoke evacuation passageway to an interconnection port of the electrosurgical instrument.

Further, the method embodiment may include the steps of interconnecting a distal end of a gas conduit to the interconnection port, and interconnecting a proximal end of the gas conduit to a vacuum generator. In turn, the vacuum generator may be operated to initiate the drawing step, i.e. to draw gas into the open passageway of the light tunnel of the light tunnel member at the distal end thereof, then through the smoke evacuation passageway and gas conduit. As may be appreciated, the gas may comprise smoke generated at a surgical tissue site and the vacuum generator may be provided so as to filter or otherwise remove smoke constituents from the surgical environment.

In addition to the noted features, the method embodiment may also include the various additional features described above and hereinbelow in relation to hand-held electrosurgical instruments.

In a further embodiment, an apparatus is provided that is interconnected or interconnectable to a hand-held electrosurgical instrument and comprises a light tunnel member, interconnected or interconnectable to the housing of the hand-held electrosurgical instrument so as to extend away from a distal end of a housing in a first direction and define a light tunnel therethrough for receiving and directing light emitted by at least one light source of the hand-held electrosurgical instrument through the light tunnel and out of a distal end of the light tunnel member. The apparatus may further include an open passageway that extends proximally from the distal end of the light tunnel member about and along at least a portion of an electrosurgical electrode of the hand-held electrosurgical instrument (e.g. an electrode supportably interconnected to and extending away from a distal end of the housing in the first direction). A proximal end of the open passageway may be fluidly interconnectable to a vacuum generator to draw gas through the distal end of the open passageway. In some implementations, the light tunnel member may be provided so that the light tunnel extends along at least a majority of a length of the electrosurgical electrode that extends distally from the housing of the hand-held electrosurgical instrument.

The apparatus may further include a tubular member adjoined to the light tunnel member and defining a smoke evacuation passageway fluidly interconnected to and extending proximally from the proximal end of the open passageway. In some embodiments, the tubular member may comprise a port located at a proximal end of the smoke evacuation passageway, wherein the port is fluidly interconnectable to a vacuum generator. In the later regard, the apparatus may be provided to include a gas conduit having a distal end interconnected or interconnectable to the port and having a proximal end interconnectable to a vacuum generator.

In some implementations, the tubular member may include a concave outer surface portion configured to conformally engage and extend along an outer surface portion (e.g. a convex outer surface portion) of the housing of the hand-held electrosurgical instrument. In some arrangements, the light tunnel member may include at least one clip member for selective interconnection of the light tunnel member to and disconnection of the light tunnel member from the housing of the hand-held electrosurgical instrument. In one embodiment, the apparatus may include a first clip member adjoined to and extending proximally from the light tunnel member for selective interconnection of the light tunnel member to and disconnection of the light tunnel member from the housing of the hand-held electrosurgical instrument, and a second clip member adjoined to and extending laterally from a proximal end of the tubular member for selective interconnection of the tubular member to and disconnection of the light tunnel member from the housing of the hand-held electrosurgical instrument.

In some arrangements, a proximal end portion of the light tunnel member may extend over at least a portion of the light source(s) of the hand-held electrosurgical instrument. Further, the proximal end portion of the light tunnel member may be light transmissive and configured so that a portion thereof abuts at least a portion of the light source(s).

Additional features and advantages of the present invention will become apparent upon consideration of the further description that follows.

BRIEF DESCRIPTION OF THE DRAWINGS

FIG. 4A is a top view of an embodiment of the hand-held electrosurgical instrument of FIG. 1, without the adjoined light tunnel member/tubular member thereof.

FIG. 4B is a side cross-sectional view of the hand-held electrosurgical instrument of FIG. 1, without the adjoined light tunnel member/tubular member thereof, taken along the cross section shown in FIG. 4A.

FIG. 6A is a top view of another embodiment of a hand-held electrosurgical instrument including a light tunnel member adjoined to a housing.

FIG. 6B is a side cross-sectional view of the hand-held electrosurgical instrument of FIG. 6A, taken along the cross section shown in FIG. 6A.

DETAILED DESCRIPTION

Figure 1:
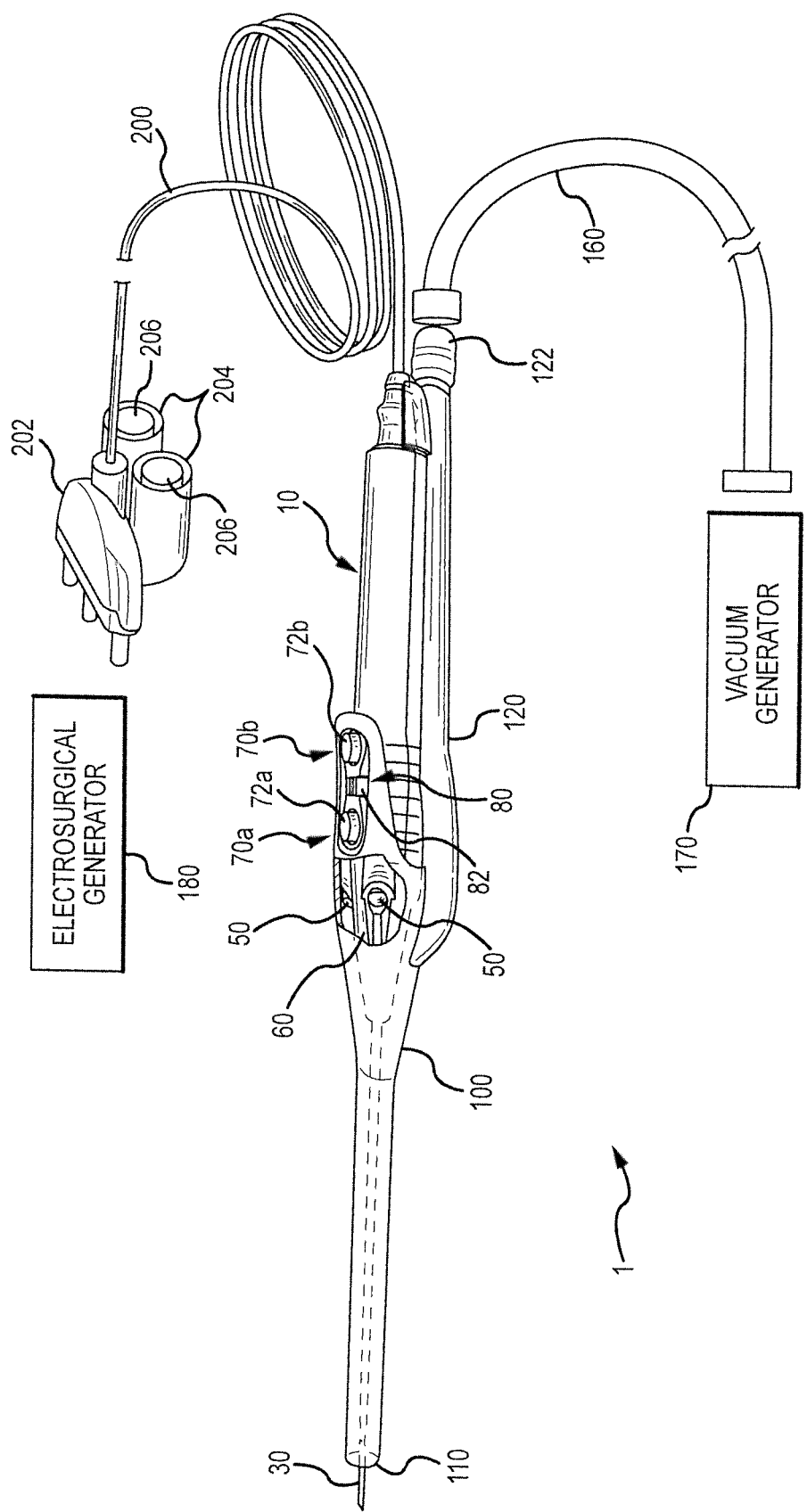
FIG. 1 illustrates an embodiment of a hand-held electrosurgical instrument including a light tunnel member, an adjoined tubular member for smoke evacuation, and a housing, with a portion of the light tunnel member cutaway to show a distal end portion of the housing.

One embodiment of a hand-held electrosurgical instrument 1 is illustrated in FIG. 1. The hand-held instrument 1 may include an elongated housing 10 configured for hand-held use, an elongated electrosurgical electrode 30 supportably interconnected to and extending from a distal end of the housing 10 in a first direction, and a plurality of light sources 50 supportably interconnected to the housing 10 for emitting light in the first direction. For example, three light sources 50 may be disposed at circumferentially offset locations about a longitudinal axis of the housing 10 wherein said circumferentially offset locations are offset by at least 90° relative to one another (e.g. 120° offset). As shown, the light sources 50 may be located about a tapered nose 60 provided at a distal end of housing 10.

The light sources 50 may each emit a light beam having a center axis parallel to or substantially parallel to (e.g. within 20°) a central axis of the electrosurgical electrode 30. In turn, the central axis of the electrosurgical electrode 30 may be aligned with a parallel to a longitudinal axis of the housing 10.

The hand-held instrument 1 may also include a light tunnel member 100 interconnected to and extending distally away from the distal end of the housing 10 in the first direction, and defining a light tunnel for receiving and directing light emitted by light sources 50 through the light tunnel and out of a distal end 110 of the light tunnel member 100 for illumination of a tissue site. As shown, the electrosurgical electrode 30 may extend through the light tunnel and project beyond the distal end 110 of the light tunnel member 100.

In the illustrated embodiment, the light tunnel member 100 may be of a tubular configuration, wherein the light tunnel comprises an open passageway that extends from the distal end 110 to a proximal end of the light tunnel member 100. As will be described, a proximal end of the open passageway may be fluidly interconnected to a vacuum generator to provide for smoke evacuation from a tissue site.

Optionally, for such purposes, hand-held instrument 1 may comprise a tubular member 120 adjoined to the light tunnel member 100 and extending proximally along a bottom side of the housing 10. The tubular member 120 may define a smoke evacuation passageway therethrough that is in fluid connection with the open passageway of the light tunnel member 100. An interconnection port 122 may be provided at a proximal end of the tubular member 120 for interconnection to a gas conduit 160.

In another arrangement, the open passageway of the light tunnel member may be in fluid communication with a smoke evacuation passageway that extends through at least a portion of housing 10 to an interconnection port that may be interconnected to the gas conduit 160. By way of example, the smoke evacuation passage may be provided by a tubular member that extends through at least a portion of housing 10 to an interconnection port that may be interconnected to the gas conduit 160, or the smoke evacuation passageway may be provided by the housing 10, as will be described in relation to FIGS. 6A, 6B and 7 hereinbelow.

In either approach, the gas conduit 160 (e.g. a length of tubing) may be interconnected to a vacuum generator 170, wherein gas (e.g. including smoke generated at a tissue site) may be drawn through the distal end 110 of the light tunnel member 100, through the smoke evacuation passageway of the tubular member 120, and through the gas conduit 160 for handling at the vacuum generator 170.

As shown in FIG. 1, the hand-held instrument 1 may further include a first signal switch 70a and a second signal switch 70b for use in controlling the selective provision of a first electrosurgical signal or a second electrosurgical signal, respectively, to the electrosurgical electrode 30. As may be appreciated, the first electrosurgical signal may be one of an electrosurgical tissue cutting signal and an electrosurgical tissue coagulation signal, and the second electrosurgical signal may be the other one of the electrosurgical tissue cutting signal and the electrosurgical tissue coagulation signal.

In one implementation, the first signal switch 70a and second signal switch 70b may each be tactile, pressure-activated switches, wherein upon the continuous manual application of pressure to and depression of biased dome 72a or biased dome 72b, respectively, electrical contact is made to provide for electrosurgical signal delivery to the electrosurgical electrode 30.

As further illustrated in FIG. 1, the hand-held instrument 1 may comprise a light switch 80 for controlling the operation of the plurality of light sources 50. In one approach, light switch 80 may be configured with a lever member 82 for selective set positioning at a center home position, a first side position, or a second side position, wherein in each of the first side position and second side position an electrical power signal is continuously provided to the plurality of light sources 50 without manual application of pressure. In the later regard, the light switch 80 may be configured so that, when lever member 82 is moved to the first side position or second side position, the lever 82 may be maintained in said position free from manual contact. Further, the light switch 80 may be provided so that, when the light switch 80 is in the center home position the light switch 80 may function as a tactile, pressure-activated switch, wherein upon the continuous manual application of pressure to and depression of lever member 82, electrical contact is made to provide for electrical power signal delivery to light sources 50. As shown, the light switch 80 may be located between and in aligned relation with the first signal switch 70a and second signal switch 70b along one side of the housing 10 (e.g. a top side).

Figure 2A:
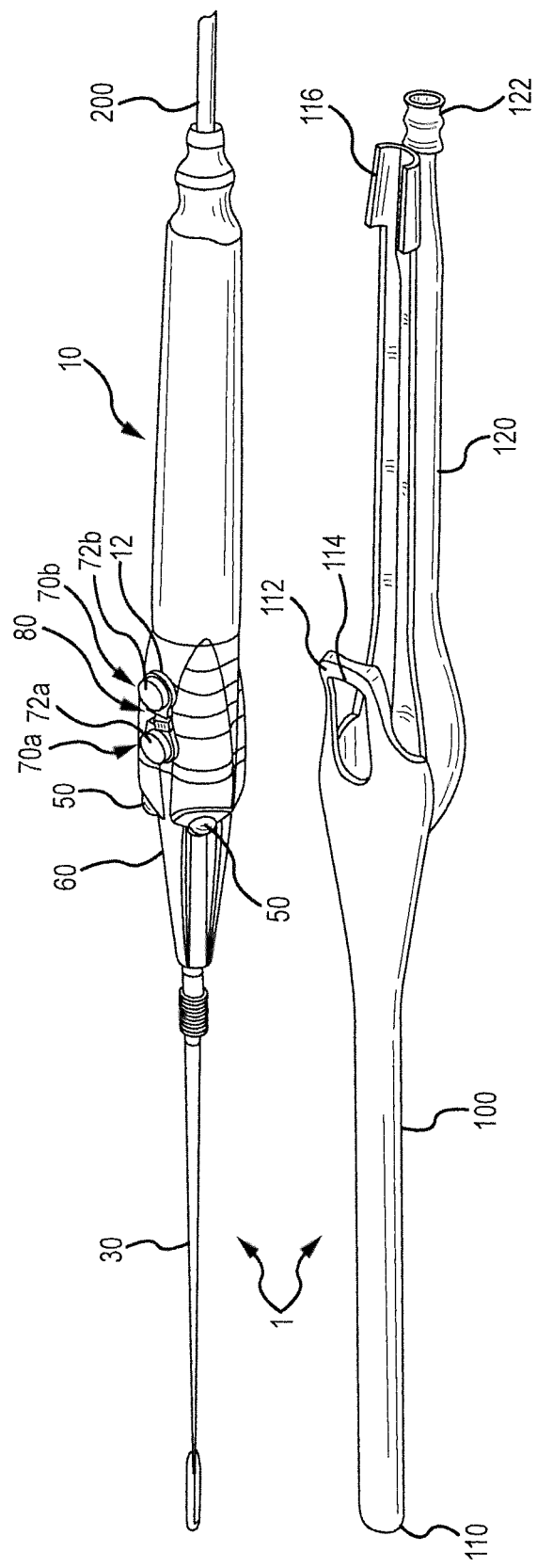
FIG. 2A illustrates an embodiment of the hand-held electrosurgical instrument of FIG. 1, with the adjoined light tunnel member/tubular member being separate from and interconnectable to the housing.
Figure 2B:
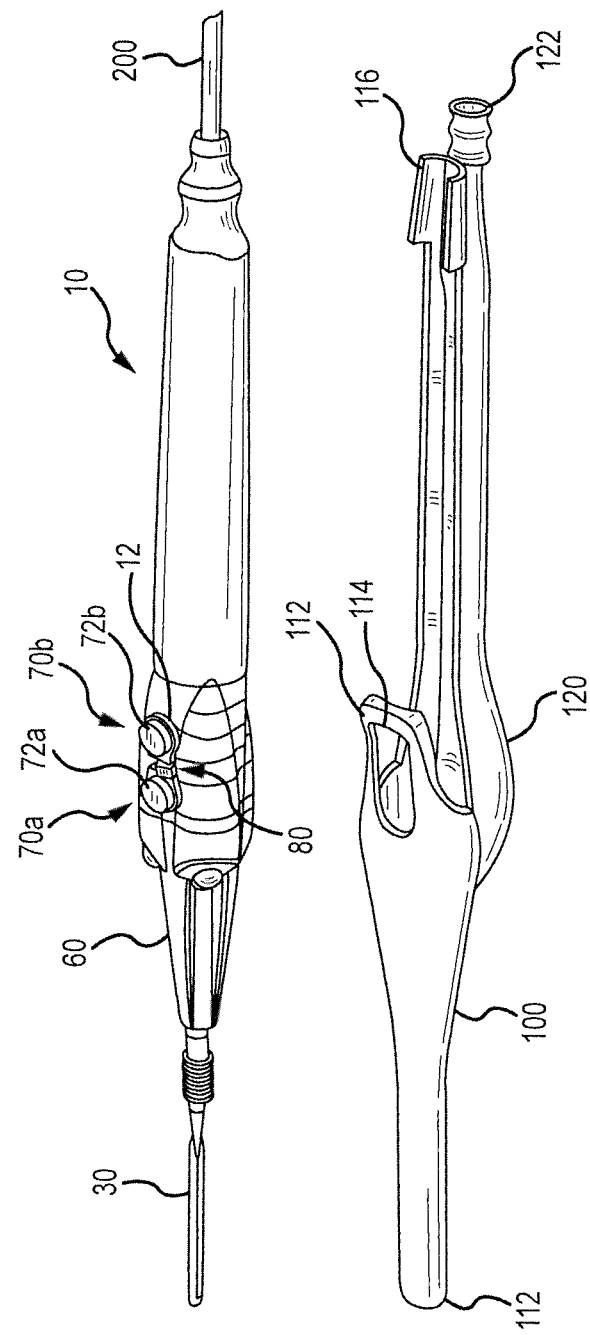
FIG. 2B illustrates another embodiment of the hand-held electrosurgical instrument of FIG. 1, with the adjoined light tunnel member/tubular member being separate from and interconnectable to the housing.

With reference to FIGS. 2A and 2B, embodiments of hand-held instrument 1 are illustrated in which an adjoined light tunnel member 100 and tubular member 100 may be provided as a separate, manipulatable apparatus that is interconnectable to and disconnectable from the housing 10 of the hand-held instrument 1. To facilitate interconnection/disconnection, the light tunnel member 100 may include a first clip member 112, adjoined to and extending proximally from the light tunnel member 100, for selective interconnection of the light tunnel member 100 to the housing 10. More particularly, the first clip member 112 and a distal end portion of the tubular member 120 may be configured to receive a distal end portion of the housing 10 therebetween to facilitate retentive interconnection of the housing 10 and light tunnel member 100. Housing 10 may include an outwardly projecting lip 12 for positioning through a slot 114 provided by the first clip member 112. As shown in FIGS. 2A and 2B, the lip 12 may be configured to extend about the first and second signal switches 70a, 70b and light switch 80, and the slot 114 may be configured to receive the entirety of the lip 12 therethrough, wherein the lip 12 abuts the periphery of 114 to restrict relative movement.

As further illustrated in FIGS. 2A and 2B, the tubular member 120 may include a second clip member 116, adjoined to and extending laterally away from the proximal end of the tubular member 120 for selective interconnection of the tubular member 120 to the housing 10. The second clip member 116 may be of a configuration sized for snap-fit engagement with a proximal end of the housing 10.

As illustrated by FIGS. 2A and 2B, the electrosurgical electrode 30 and light tunnel member 100 may be provided in varying lengths to accommodate the corresponding electrosurgical application. For example, the electrosurgical electrode 30 and light tunnel member 100 of FIG. 2A, are each longer than the electrosurgical electrode 30 and light tunnel member 100 of FIG. 2B. In each case, however, the light tunnel member 100 extends along at least a majority of a length of the electrosurgical electrode 30 that extends distally from the housing 10, and more particularly, the light tunnel member may extend along at least 70% of the length of the electrosurgical electrode that extends distally from the housing.

Reference is now made to FIGS. 3A, 3B and 3C, and FIGS. 4A and 4B which illustrate components of hand-held instrument 1 provided with housing 10. In that regard, housing 10 may comprise a top member 10a and a bottom member 10b which may be interconnected along opposing peripheral edges to define an enclosed volume. Further, as noted above, housing 10 may be provided with a nose 60 at the distal end thereof. A number of components may be located within the enclosed volume of housing 10.

In particular, the first and second signal switches, 70a, 70b and light switch 80 may be physically positioned in aligned relation relative to an electrical connection board 90 (e.g. a printed circuit board) that is disposed within the enclosed volume of housing 10. In particular, the first signal switch 70a may comprise dome 72a positioned over an upwardly biased switch member 74a that may be mounted directly to the electrical connection board 90 at a first location, and the second signal switch 70b may comprise dome 72b positioned over an upwardly biased switch member 74b that may be directly mounted to the interconnection board 90 at a second location proximal to the first location. The light switch 80 may comprise lever member 82 positioned over an upwardly biased switch member 84 that is supported by a lever cage 86 that is positioned on electrical connection board 90. To facilitate relative retentive positioning of such components, a top cover member 14a and bottom cover member 14b may be positioned above and below the electrical connection board 90, respectively, wherein the top cover member 14a and bottom cover member 14b are interconnectable about their peripheries. In turn, the interconnected top cover member 14a and bottom cover member 14b, together with the various switch members noted above, may be located within the enclosed volume of housing 10.

As further illustrated in FIGS. 3A, 3B and 3C, and FIGS. 4A and 4B, light sources 50 (e.g. light emitting diodes) may be physically interconnected to a mount 52 that is physically interconnected to the electrical connection board 90, wherein the light sources 50 are also electrically interconnected to the electrical connection board 90. Additionally, an electrode socket 92 may be physically and electrically interconnected to the electrical connection board 90. In turn, the electrosurgical electrode 30 may be physically and electrically interconnected to the electrode socket 92. In that regard, a proximal end of the electrosurgical electrode 30 may be located through a central passageway of the nose 60 and inserted into the electrode socket 92. The nose 60 may include proximal projections 62 having corresponding apertures 64 configured for snap fit engagement with projecting tabs 16 provided on the top cover member 14a and bottom cover member 14b.

The nose 60 may be configured to have a proximal end that conformally adjoins the distal ends of the top and bottom members 10a, 10b, and a plurality of outward facing channel portions that extend distally from the proximal end to a distal end, wherein the channel portions are defined by a plurality of landings that project outward from a cylindrical core portion and that taper down from the proximal end of the nose to the distal end thereof. In turn, the nose 60 may include a plurality of apertures 66 at the proximal ends of the channel portions for receiving the plurality of light sources 50 in on-to-one relation therethrough.

Figure 3A:
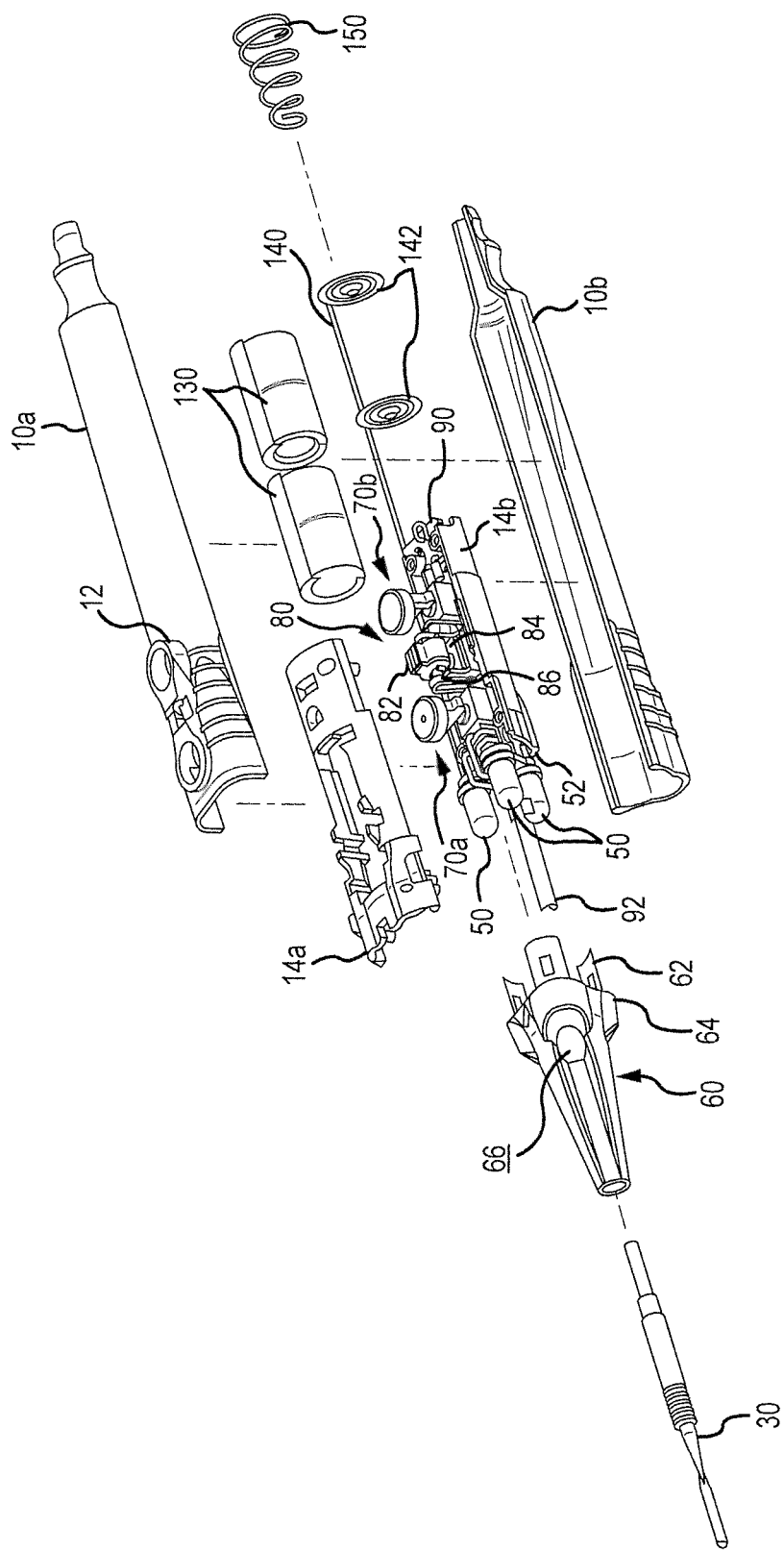
FIGS. 3A, 3B, and 3B are exploded views of components housed in the housing of the hand-held electrosurgical instrument of FIG. 1.
Figure 3B:
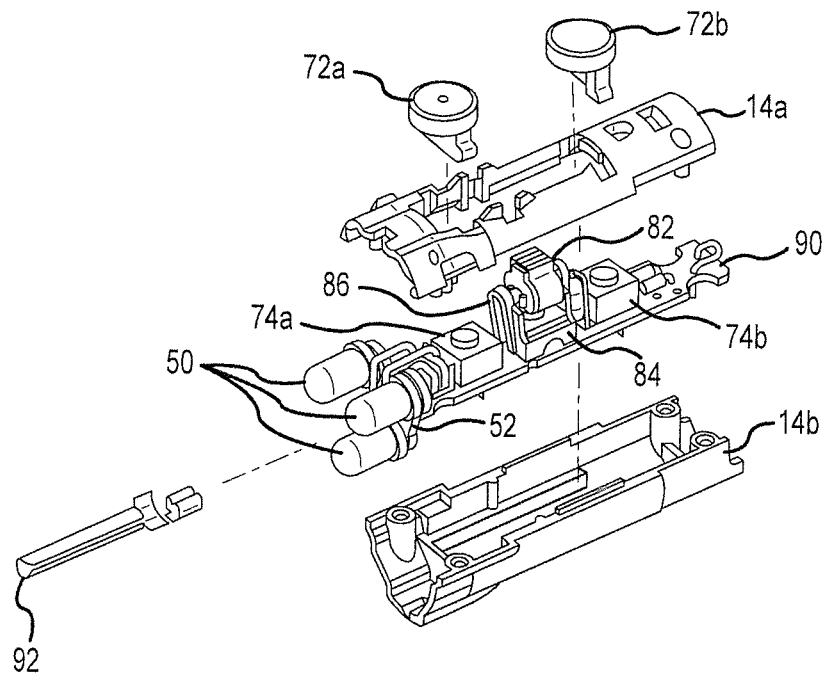
Figure 3C:
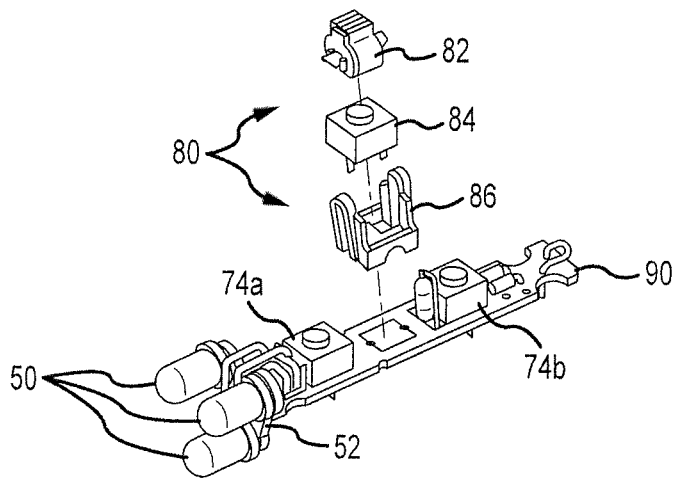

As further illustrated in FIGS. 3A and 4B, two batteries 130 may be disposed in aligned relation within a proximal end of the housing 10. An electrical contact member 140 may be provided with electrical contact portions 142 disposed for contact engagement with end terminals of the batteries 130, wherein the electrical contact member 140 is also electrically interconnected to the electrical interconnection board 90. As shown, a spring member 150_is provided to maintain contact engagement between the contact portions 142 and terminals of the batteries 130.

With further reference to FIG. 1, the hand-held electrosurgical instrument may also include electrical cabling 200 that extends proximally from the distal end of housing 10. The cabling 200 may comprise a plurality of conductors (e.g. three wires) defining a first electrical signal line and a plurality of conductors (e.g. two wires) defining a second electrical signal line. The first electrical signal line is interconnected to a three-prong plug 202 at a proximal end for electrical interconnection with an electrosurgical generator 180, and a distal end electrically interconnectable to the electrosurgical electrode 30. In the later regard, the first signal switch 70a described above may be manipulatable to control on/off delivery of a first electrosurgical signal (e.g. a tissue cutting signal) from an electrosurgical generator via the first electrical signal line to the electrosurgical electrode 30. Further, second signal switch 70b described above may be manipulatable to control on/off delivery of a second electrosurgical signal (e.g. a tissue coagulation signal) from the electrosurgical generator via the first electrical signal line to the electrosurgical electrode 30. The second electrical signal line of cabling 200 may have a proximal end that is electrically connected to one or a plurality of batteries 206 (e.g. two removable/replaceable batteries shown in FIG. 1) located in battery support members 204 supportably interconnected to plug 202, and a distal end electrically interconnectable to the light source(s) 50 via the manually controllable on/off light switch 80.

Figure 5:
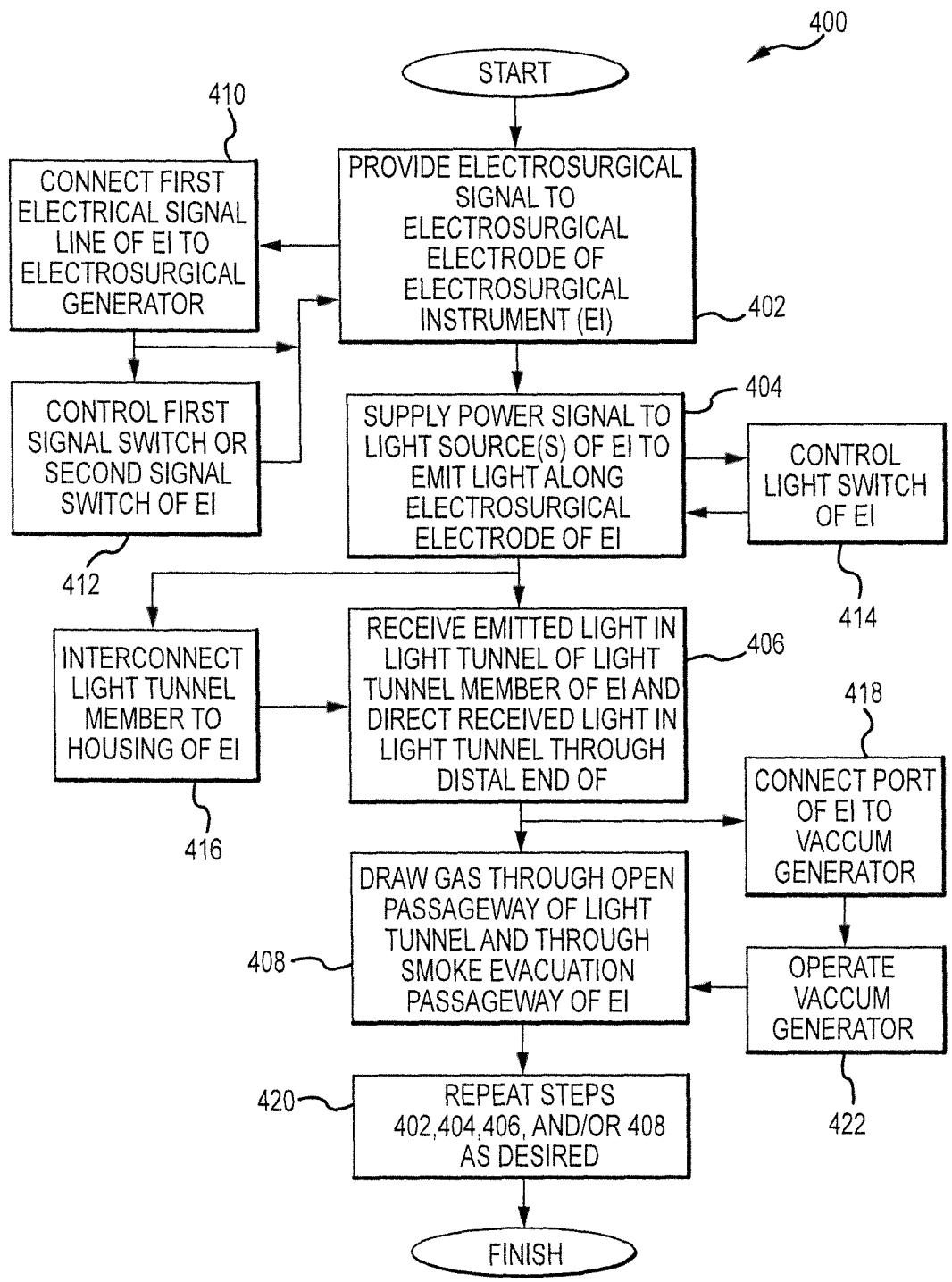
FIG. 5 illustrates steps of an embodiment of a method for operation of an electrosurgical instrument.

Reference is now made to FIG. 5 which illustrates an embodiment 400 of a method of operation of an electrosurgical instrument, e.g. hand-held electrosurgical instrument 1 described above. The method embodiment 400 may include the steps of providing an electrosurgical signal to an electrosurgical electrode of an electrosurgical instrument (Step 402), and supplying a power signal to a light source(s) of the electrosurgical instrument to emit light from the light source(s) along the electrosurgical electrode (Step 404). Further, the method embodiment 400 may include the steps of receiving the emitted light in a light tunnel of a light tunnel member of the electrosurgical instrument and directing the received light in the light tunnel through the light tunnel to a distal end of the light tunnel member (Step 406). Additionally, the method embodiment 400 may optionally include the step of drawing gas through an open passageway of the light tunnel of the light tunnel member, and in some embodiments, through a smoke evacuation passageway of the electrosurgical instrument (Step 408). As may be appreciated, Steps 402 and 404 may be occur and be repeated in any desired sequence, whether overlapping, partially overlapping or non-overlapping (Step 420).

In conjunction with the providing step (Step 402), the method embodiment 400 may include the steps of connecting a first electrical signal line of the electrosurgical instrument to an electrosurgical generator (Step 410). Further, the providing step (Step 402) may entail the step of controlling a first signal switch or a second signal switch of the electrosurgical instrument (Step 412), wherein an electrosurgical tissue cutting signal or an electrosurgical tissue coagulation signal is provided to the electrosurgical electrode.

Further, the supplying step (Step 404) may entail the step of controlling a light switch of the electrosurgical instrument (Step 414). In one approach, the electrosurgical instrument may include one or more batteries to provide the power signal. In another approach, the electrosurgical instrument may include a second electrical signal line that may be electrically interconnected to a power supply (e.g. a DC power outlet) to provide the power signal.

Prior to the receiving step (Step 406), the method embodiment 400 may include the step of interconnecting the light tunnel member to a housing of the electrosurgical instrument (Step 416). In that regard, the light tunnel member and housing may be separate structures that allow for selective use of the light tunnel member when desired. To facilitate interconnection, the light tunnel member may include a first clip member extends primarily for engagement with a distal end portion of the housing. In one approach the first clip member includes an opening for engagement with a lip that projects from an outer surface of the housing.

In further relation to the drawing step (Step 408) of the method embodiment 400, the smoke evacuation passageway of the electrosurgical instrument may be defined by a tubular member. In turn, a distal end of the smoke evacuation passageway may be fluidly interconnected to a proximal end of the open passageway of the light tunnel member. Further, a proximal end of the smoke evacuation passageway may be fluidly interconnected to an interconnection port of the tubular member. The tubular member may be adjoined to the light tunnel member for handling as a single unit. In another approach, the smoke evacuation passageway may be provided to extend through all or a portion of the housing and may be fluidly interconnected to an interconnection port at a proximal end of the housing.

In conjunction with the drawing step (Step 408) an interconnection port as described above may be fluidly interconnected to a vacuum generator via a gas conduit (e.g. a length of tubing) (Step 418). In turn, the vacuum generator may be operated (Step 422), wherein the gas may be drawn through the open passageway of the light tunnel through the smoke evacuation passageway, and through the gas conduit, for handling, at the vacuum generator.

Figure 7:
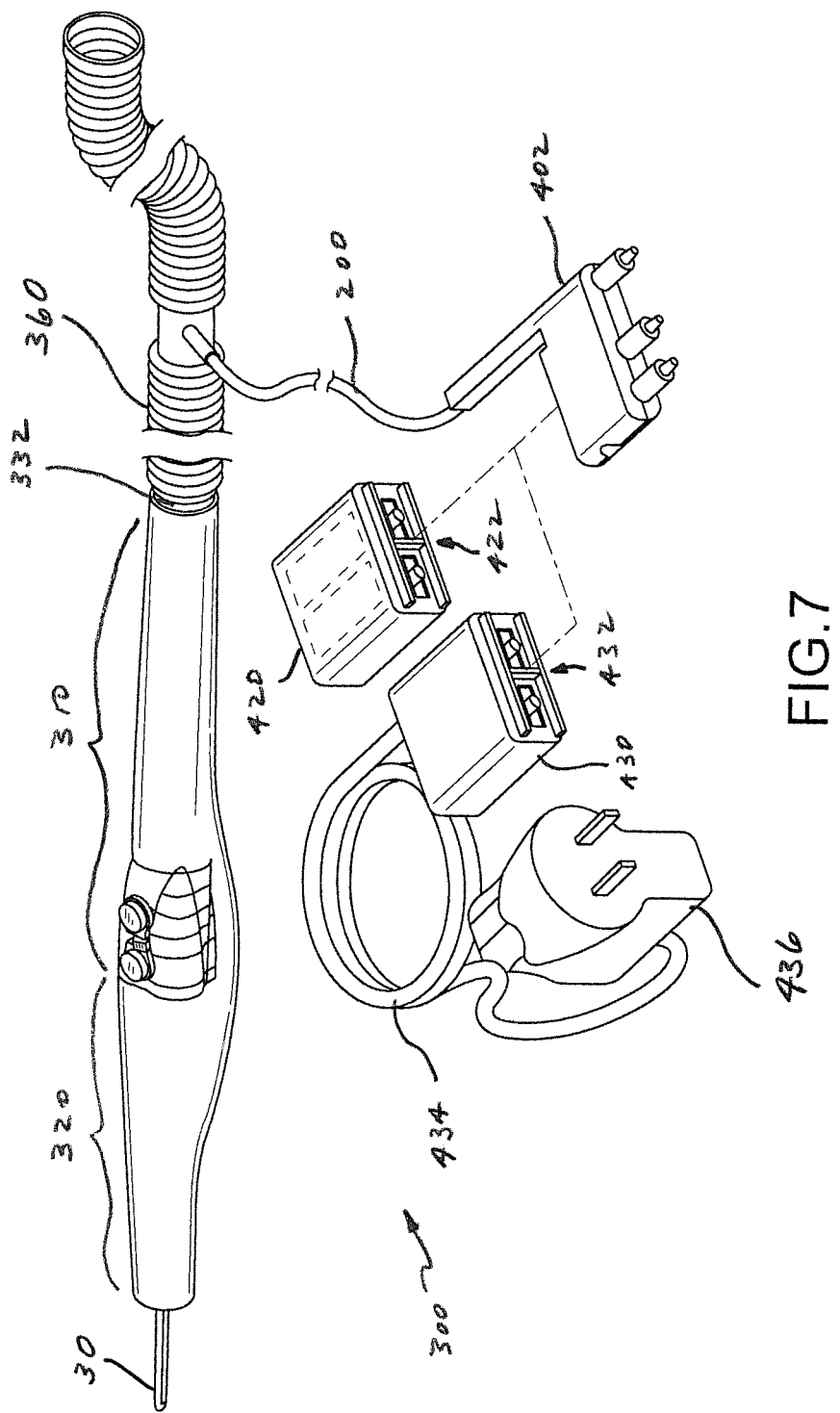
FIG. 7 is another view of the hand-held electrosurgical instrument of FIG. 6A, illustrating additional electrical signal line and smoke evacuation features.

Reference is now made to FIGS. 6A, 6B and 7 which illustrate another embodiment of a hand-held electrosurgical instrument 300. The hand-held instrument 300 includes a number of components in common with the components shown and described above in relation to hand-held instrument 1. As such, the common components are shown in FIGS. 6A, 6B and 7 with common reference numerals, and the description of such components provided above in relation to hand-held instrument 1 applies to the hand-held instrument 300.

As illustrated, the hand-held instrument 200 may include an elongated housing 310 configured for hand-held use, an elongated electrosurgical electrode 30 supportably interconnected to and extending from a distal end of the housing 310 in a first direction, a plurality of light sources 50 supportably interconnected to the housing 310 for emitting light in the first direction (e.g. three light sources disposed at circumferentially offset locations about a longitudinal axis of the housing 310 and electrode 30—locations offset by at least 90° relative to one another (e.g. 120° offset)), and a light tunnel member 320 interconnected to and extending distally away from the distal end of the housing 310 in the first direction. The light tunnel member 320 may define a light tunnel for receiving and directing light emitted by the light sources 50 through the light tunnel and out of a distal end 322 of the light tunnel member 320 for illumination of a tissue site. As shown, the electrosurgical electrode 30 may extend through the light tunnel of the light tunnel member 320 and project beyond the distal end 322 of the light tunnel member 320.

The light tunnel member 320 may be of a tubular configuration, wherein the light tunnel comprises an open passageway that extends from the distal end 322 to a proximal end of the light tunnel member 220 that is fluidly interconnected to a distal end of a smoke evacuation passageway 312 that is defined by and extends through the housing 310 from a distal end to a proximal end thereof. In that regard and unlike hand-held instrument 1, hand-held instrument 300 does not include a nose 60 or batteries 130, described above in relation to hand-held instrument 1.

As shown in FIG. 6B, the housing 310 and light tunnel member 320 may be defined together by a top member 310a and a bottom member 310b that each extend from the distal end 322 of the light tunnel member 320 to a proximal end of the housing 310. As may be appreciated, the top member 310a and bottom member 310b may be interconnected along opposing peripheral edges to define the open passageway 312 of the light tunnel of the light tunnel member 320 and the smoke evacuation passageway 312 through the housing 310. In turn, the hand-held instrument 300 may include an interconnection port 332 that may be interconnected or interconnectable to a gas conduit 360, as shown in FIG. 7, wherein a proximal end of the gas conduit 360 may be interconnected to a vacuum generator 170, as shown in FIG. 1. In turn, upon operation of the vacuum generator 170, gas (e.g. including smoke generated at a tissue site) may be drawn in to the distal end 322 of the light tunnel member 320 and open passageway thereof, through the smoke evacuation passageway 312 of the housing 310, and through the gas conduit 170 for handling at the vacuum generator 170.

As shown in FIGS. 6B and 7, a proximal end of electrical cabling 200 may extend in to hand-held instrument 200 for electrical interconnection with various components within hand-held instrument 200, as described above in relation to hand-held instrument 1. In particular, a first electrical signal line comprising a plurality of conductors (e.g. three wires) may be interconnected for the selective, switch-controlled provision of electrosurgical signals to electrode 30, and a second electrical signal line comprising a plurality of conductors (e.g. two wires) may be interconnected for the selective, switch-controlled provision of DC power to the light sources 50. As shown in FIG. 7, the electrical cabling 200 may extend rearwardly from housing 310 through gas conduit 360, wherein a distal end portion of the electrical cabling 200 may exit the gas conduit 360 and may be interconnected at a distal end to a three-prong plug 402. In that regard, different ones of the plurality of conductors of the first electrical signal line within electrical cabling 200 may be interconnected with different ones of the three prongs of the plug 402, wherein the plug 402 may be electrically interconnected to an electrosurgical generator 180, as shown in FIG. 1, to deliver electrosurgical signals to electrode 30, as described above in relation to hand-held instrument 1.

Further, the plurality of conductors comprising the second electrical signal line within electrical cabling 200 may be disposed within plug 402 for selective engagement with and disengagement from either a port end 422 of a battery pack 420 or a port end 432 of an end member 430 interconnected via cabling 434 to an AC to a DC adapter plug 436 that may be plugged in to an AC wall socket. Battery pack 420 may supportably house one or a plurality of removable/replaceable batteries (e.g. two batteries shown by phantom lines) for the provision of DC power. As illustrated, the port end 422 of the battery pack 420 and the port end 432 of the end member 430 may be commonly configured, wherein either of the end ports 422, 432 may be physically interconnected to a back side of the plug 402 and electrically interconnected to the conductors of the second electrical signal line presented at the back side of plug 402.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain known modes of practicing the invention and to enable others skilled in the art to utilize the invention in such or other embodiments and with various modifications required by the particular application(s) or use(s) of the present invention. It is intended that the appended claims be construed to include alternative embodiments to the extent permitted by the prior art.

What is claimed is:

1. A hand-held electrosurgical instrument, comprising:
   a housing configured for hand-held use;
   an electrosurgical electrode supportably interconnected to and extending away from a distal end of the housing in a first direction;
   at least three light sources supportably interconnected to said housing for emitting light in said first direction along the electrosurgical electrode, wherein said at least three light sources are disposed at circumferentially offset locations about a longitudinal axis of the housing, and wherein each of said at least three light sources emits a corresponding light beam having a corresponding center axis parallel or substantially parallel to a central axis of the electrosurgical electrode; and,
   a light tunnel member, interconnected or interconnectable to said housing, extending away from the distal end of the housing in the first direction and defining a light tunnel therethrough for receiving and directing light emitted by said at least three light sources through the light tunnel and out of a distal end of the light tunnel member, wherein said electrosurgical electrode extends through at least a portion of said light tunnel of the light tunnel member, and wherein a proximal end portion of the light tunnel member is light transmissive and configured to extend over and abut at least a portion of each of said at least three light sources.

2. A hand-held electrosurgical instrument as recited in claim 1, wherein the electrosurgical electrode extends through and beyond the distal end of the light tunnel member.

3. A hand-held electrosurgical instrument as recited in claim 2, wherein the light tunnel of the light tunnel member extends along at least a majority of a length of the electrosurgical electrode that extends distally from the housing.

4. A hand-held electrosurgical instrument as recited in claim 1, wherein the light tunnel comprises an open passageway that extends proximally from the distal end of the light tunnel member, wherein a proximal end of the open passageway is fluidly interconnectable to a vacuum generator.

5. A hand-held electrosurgical instrument as recited in claim 4, further comprising:

a smoke evacuation passageway fluidly interconnected to and extending proximally from the open passageway of the light tunnel of the light tunnel member.

6. A hand-held electrosurgical instrument as recited in claim 5, further comprising:
a tubular member at least partially defining said smoke evacuation passageway.

7. A hand-held electrosurgical instrument as recited in claim 5, wherein said tubular member is adjoined to said light tunnel member for handling as a single unit.

8. A hand-held electrosurgical instrument as recited in claim 7, wherein said tubular member includes a concave outer surface portion configured to conformally engage and extend along an outer surface portion of the housing.

9. A hand-held electrosurgical instrument as recited in claim 7, wherein the light tunnel member further comprises:
at least one clip member for selective interconnection of the light tunnel member to the housing.

10. A hand-held electrosurgical instrument as recited in claim 7, further comprising:
a first clip member, adjoined to and extending proximally from the light tunnel member, for selective interconnection of the light tunnel member to the housing; and
a second clip member, adjoined to and extending laterally away from a proximal end of tubular member, for selective interconnection of the tubular member to the housing.

11. A hand-held electrosurgical instrument as recited in claim 5, wherein at least a portion of said smoke evacuation passageway extends through at least a portion of said housing.

12. A hand-held electrosurgical instrument as recited in claim 5, further comprising:
a port located at a proximal end of said smoke evacuation passageway.

13. A hand-held electrosurgical instrument as recited in claim 12, further comprising:
a gas conduit having a distal end interconnected or interconnectable to said port, and having a proximal end interconnectable to a vacuum generator.

14. A hand-held electrosurgical instrument as recited in claim 1, wherein said at least three light sources comprises N light sources, wherein N≥3 and the circumferentially offset locations of adjacent ones of the N light sources are offset by at least A°=180°/N−1.

15. A hand-held electrosurgical instrument as recited in claim 14, wherein the proximal end portion of the light tunnel member extends over an entirety of each of said at least three light sources.

16. A hand-held electrosurgical instrument as recited in claim 1, wherein the proximal end portion of the light tunnel member extends over an entirety of each of said at least three light sources.

17. A hand-held electrosurgical instrument as recited in claim 1, further comprising: at least one battery operatively interconnectable to said at least three light sources, wherein said at least three light sources are operable to emit light from interconnection to an external energy source.

18. A hand-held electrosurgical instrument as recited in claim 17, wherein said at least one battery is supportably disposed within said housing.

19. A hand-held electrosurgical instrument as recited in claim 17, further comprising: an electrical signal line having a distal end electrically interconnectable to said at least three lights sources, and having a proximal end electrically interconnected or interconnectable to said at least one battery; and a battery support member physically interconnected to said electrical signal line at said proximal end thereof, wherein said at least one battery is supportably positionable within and removable from said battery support member.

* * * * *